United States Patent [19]

Stern et al.

[11] Patent Number: 5,162,199
[45] Date of Patent: Nov. 10, 1992

[54] NEISSERIA-SPECIFIC DNA PROBE

[75] Inventors: Anne Stern, Penzberg; Karin Wolff, Germering, both of Fed. Rep. of Germany

[73] Assignee: Boehringer Mannheim GmbH, Mannheim, Fed. Rep. of Germany

[21] Appl. No.: 531,226

[22] Filed: May 31, 1990

[30] Foreign Application Priority Data

Jun. 22, 1989 [DE] Fed. Rep. of Germany ....... 3920492
Aug. 2, 1989 [DE] Fed. Rep. of Germany ....... 3925613

[51] Int. Cl.$^5$ .................... C12G 1/68; C12P 19/34; C12N 11/02; C07H 15/12
[52] U.S. Cl. .................................... 435/6; 435/91; 435/177; 435/822; 435/871; 536/27; 935/78; 935/88
[58] Field of Search ............ 435/6, 27, 91; 436/501, 436/811; 935/9, 16, 17, 78, 88

[56] References Cited

U.S. PATENT DOCUMENTS

| | | | |
|---|---|---|---|
| 4,358,535 | 11/1982 | Falkow | 435/5 |
| 4,446,230 | 5/1984 | Zubrxycki | 435/6 |
| 4,900,659 | 2/1990 | Lo et al. | 435/6 |
| 5,047,523 | 9/1991 | Woods et al. | 536/27 |

FOREIGN PATENT DOCUMENTS 0238332 3/1987 European Pat. Off. .
0337896 10/1989 European Pat. Off. ............... 435/6

89/03891 5/1989 Int'l Pat. Institute .

OTHER PUBLICATIONS

Stern et al. (I) Cell 47(1) 61-71 (1986).
Pohlner et al. Nature 325:458-62 (1987).
Haas et al. Cell 44:107-115 (1986).
Stern et al. (II) Chem. Abstract vol. 112(13):May 7 (1990) Abs. No. 112:173137j.
Perry et al. Gene 60:85-92 (1987).
Totten et al. J. Infec. Disease 148(3):462 (1983).
Dinegan et al. Mol. and Cell Probes 3:13 (1989).
Kolberg et al. Mol. and Cell Probes 3:59 (1989).
Halter et al. Embo J. 3(7) 1595-01 (1984).
Stern et al. Cell 37:447-56 (1984).

*Primary Examiner*—Robert A. Wax
*Assistant Examiner*—Miguel Escallon
*Attorney, Agent, or Firm*—Nikaido, Marmelstein, Murray & Oram

[57] ABSTRACT

A Neisseria-specific DNA probe is chosen from the group of the oligonucleotides Opa 1, Opa 2, Opa 3, P III, Pil 1, IgA 1 and IgA 2 or from sequences complementary to these and it can have up to 5 further nucleotides at the 5' and/or 3' end. The probe is suitable for the detection of at least one of the pathogenic Neisseria species *N. gonorrhoeae* and *N. meningitidis* under hybridization conditions by the detection of the hybrid formation.

27 Claims, No Drawings

NEISSERIA-SPECIFIC DNA PROBE

DESCRIPTION

The invention concerns Neisseria-specific DNA probes and a method for the detection of at least one of the pathogenic Neisseria species N. gonorrhoeae and N. meningitidis.

The species Neisseria is a group of closely related gram-negative diplococci to which belong pathogenic as well as non-pathogenic species.

The pathogenic species are N. gonorrhoeae and N. meningitidis. In addition there are several non-pathogenic species which are part of the physiological flora of the upper respiratory tract. N. gonorrhoeae is the pathogen of gonorrhoea which is still today the most frequent notifiable infectious disease in the world (World Health Statistics Annual. (1979), Geneva, WHO). Every year several million cases are registered in the USA alone; if not treated, this illness can lead to serious secondary diseases such as e.g. prostatitis, peritonitis, and arthritis. The course of the infections is often asymptomatic at first, whereby many carriers unknowingly contribute to the spreading of the disease.

The method used up to now for the diagnosis of the disease is dependent on the sex of the patient and on the symptoms: a culture is prepared which has to be incubated for 24 to 48 hours and the cultured organisms are tested using the gram-staining method, the degradation of carbohydrate, coagglutination, fluorescence antibody screening etc. In a disseminating gonorrhoea blood cultures ought to be prepared or samples of the affected regions have to be taken which is a very laborious procedure.

N. meningitidis is one of the pathogens of bacterial meningitis. About 20 % of all contagious meningitises are caused by meningococci. One requirement for the onset of the disease is the colonisation of the pharynx with virulent meningococci (primarily of the serotypes A, B or C) as well as the lack of sufficient power of resistance of the immune system.

A reliable diagnosis of meningitis is only possible up to now bacteriologically. A crucial step in this is again the preparation of a culture. In addition a differential diagnosis is carried out in order to differentiate from other gram-negative, oxidase-positive cocci: test for sugar metabolism, agglutination reactions with serogroup-specific antibodies etc.

Thus in the majority of cases the diagnostic detection of both pathogenic Neisseria species requires the preparation of a culture which needs an incubation time of at least 24 hours. Moreover, the culture, in particular of N. gonorrhoeae, is very difficult. Selective media are used for the culture of both species on which, however, non-pathogenic Neisseria such as e.g. N. lactamica can also grow. For this reason there is a risk of mistake which can only be excluded by exact and time-consuming biochemical differentiation. Attempts have therefore already been made to develop diagnostic tests which enable the rapid and specific detection of the pathogenic Neisseria species. One possibility for this appeared, from the point of view of speed, to be provided by the technique of nucleic acid hybridization.

It has therefore already been attempted to establish methods of detection for N. gonorrhoeae with the aid of this technique, whereby one has concentrated, above all, on the following nucleic acid probes: sequences which are complementary to rRNAs (EP-A 0 272 009), sequences on cryptic plasmids which occur primarily in N. gonorrhoeae (Totten et al., J. Inf. Dis. 148 (1983), 462 and Perin et al., J. Inf. Dis. 152 (1986), 59) and sequences of unknown function which can be found using complicated screening methods (EP-A 0 237 737).

However, all these approaches are confronted by the problem that the Neisseria species represents a group of closely related organisms which are very difficult to differentiate genetically from one another. The degree of genetic relationship is extraordinarily high especially between N. gonorrhoeae and N. meningitidis. Thus DNA/DNA hybridizations of the chromosomal DNA's indicate a degree of homology of 93 % (Hoke and Vedros, Ing. J. Sys. Bact. 32 (1982), 57). The strikingly strong homology is, however, not restricted to the pathogenic Neisseria species but rather it could be shown, e.g. by transformation experiments and DNA hybridization, that N. meningitidis and N. lactamica are also closely related to one another.

The object of the present invention was therefore to provide specific detection probes which enable the differentiation between pathogenic and non-pathogenic Neisseria species by means of the technique of DNA hybridization and thus enable a qualitative as well as quantitative detection of the pathogenic species.

This object is achieved according to the present invention by a DNA probe specific for pathogenic Neisseria species which is chosen from the group of the oligonucleotides Opa 1, Opa 2, Opa 3, PIII, Pil 1, IgA 1 and IgA 2. The DNA sequences of the nucleotides according to the present invention are shown in Table 1.

TABLE 1

| Notation | Sequence 5' —> 3' |
|---|---|
| PIII | ccatttccctgtct |
| Pil 1 | aaccggctgtccgc |
| IgA 2 | cggacggtgcacaa |
| Opa 1 | ctgcgctgcggaag |
| Opa 2 | gcggcccgtatgtg |
| Iga 1 | cggtattacccggt |
| Opa 3 | gcagcccgtattat |

These DNA probes according to the present invention correspond to particular parts of genes for Neisseria proteins which occur almost exclusively in pathogenic species. These are the proteins IgA 1-protease (Pohlner et al., Nature 235 (1987), page 458), Pilin (Haas et al., Cell 44 (1986), page 107, Perry et al., Gene 60 (1987), page 85), protein II (Stern et al., Cell 47 (1986):61, Stern et al., Mol. Microbiol. 1 (1987) 5), protein III (Gotschlich, J. Exp. Med. 165 (1987), page 471).

Some of the genes for the proteins mentioned have already been used in hybridization studies in which a plasmid was used which contained the complete gene of the corresponding protein and partly also flanking sequences of the bacterial genome (Aho et al., Infect. Immun. 55 (1987), page 1009, Horn et al., Diagn. Microbiol. Infect. Dis. 4 (1986), page 101). However, neither a specific detection of the pathogenic species nor a differentiation between both the pathogenic species was successful with any of these test probes.

Surprisingly, however, by using the probes according to the present invention, which correspond to particular parts of the genes mentioned, one succeeded in distinguishing extraordinarily specifically pathogenic from non-pathogenic Neisseria species as well as from non-Neisseria species and in addition with some of the probes it was possible to distinguish specifically between the two species *N. gonorrhoeae* and *N. meningitidis*.

The probes according to the present invention are at least 14 nucleotides long and can have further nucleotides, preferably up to 5 nucleotides, at their 5' and/or 3' ends. A total length of 40 nucleotides should not be exceeded.

In this connection, the additional nucleotides can be any nucleotides, however, these nucleotides are preferably the same as those nucleotides at the 5' or 3' end in the corresponding protein.

Oligonucleotides which are particularly preferred according to the present invention, Opa1*, Opa2*, Opa3*, PIII*, Pil1*, IgA1* and IgA2*, are specified in Table 2 in the Example.

The Neisseria-specific DNA probes according to the present invention can, furthermore, be present in different forms. Thus, they can be present as single-stranded oligonucleotides, hybridized with a complementary oligonucleotide as double-stranded DNA fragments, or associated with other sequences which have no homology to the DNA from Neisseria species e.g. cloning vectors. In this connection, the possibility arises, on the other hand, for a differentiation in single-stranded vectors such as e.g. M13 and double-stranded vectors such as e.g. pBR322 derivatives. However, in addition, the individual oligonucleotides can also preferably be coupled to one another in a single or double-stranded form so that two or more of the oligonucleotides are present in one vector. When using the double-stranded forms the probe is separated by denaturation into the single-strands before the actual test reaction.

In a further preferred embodiment of the invention the nucleic acid probes are labelled. This is, in principle, possible by means of all well-known types of label for nucleic acids, such as radioactive labelling, namely the incorporation of radioactive isotopes, or else, preferably, by means of non-radioactive labelling, e.g. via the incorporation of modified nucleotides.

A further object of the invention is a method for the detection of at least one of the pathogenic Neisseria species *N. gonorrhoeae* and *N. meningitidis* using a hybridizing probe under hybridization conditions and detection of the hybrid formation which is characterized in that one of the DNA probes according to the present invention is used for the specific detection. The DNA probes according to the present invention hybridize with sections of the chromosomal Neisseria DNA which code for the pathogenicity factors as well as with RNA, namely that portion of the mRNA which represents the transcription product of the pathogenicity factor genes. It is therefore possible in the method according to the present invention to quantitatively and qualitatively determine the presence and absence of the pathogenic Neisseria species. Furthermore, by means of the method according to the present invention it is also possible to distinguish between the two pathogenic Neisseria species. In order to detect both pathogenic species the probes PIII, Pil 1, IgA 2 and Opa 1 and preferably the probes PIII*, Pil1*, IgA2* and Opa1* are used according to the present invention of which, in turn, the probes PIII, Pil 1, PIII*, Pil1*, IgA2 and IgA2* are particularly preferred. With the probes Opa 1 and Opa 1* hybridizations with non-pathogenic Neisseria species can result to a slight extent as can be inferred from Table III. However, these two probes are also well-suited for a qualitative test in which, if the test result is positive, it could be checked, if desired, with one of the other probes.

For the detection of *Neisseria gonorrhoeae* alone or in order to distinguish from *Neisseria meningitidis*, one of the probes IgA 1 and Opa 2 and preferably IgA1* and Opa2* are used according to the present invention, whereby IgA 1 and IgA1* are, in turn, particularly preferred on the basis of the lack of interaction with non-pathogenic Neisseria species.

The probe Opa 3 and preferably Opa3* is used according to the present invention for the detection of *Neisseria meningitidis* alone.

The detection by means of hybridization with at least one of the probes according to the present invention can be carried out according to well-known methods for the detection of nucleic acids by means of hybridization. The DNA-DNA hybridization was first described by Southern in J. Mol. Biol. 98 (1975) 503 and subsequently developed further. All suitable nucleic acid hybridization methods can be used such as e.g. solid-phase hybridization, hybridization in solution, sandwich hybridization, two-component hybridization. The detection is then carried out via either the radioactive or non-radioactive label of the probe.

According to the present invention, by use of particular Neisseria-specific DNA probes, a rapid and reliable test can be successfully carried out for the presence of pathogenic Neisseria species in body fluids and smears and thus for an infection of the patient. A bacterial culture is not necessary for this and also it avoids an additional test in order to distinguish from other bacteria. On the contrary, by means of the method according to the present invention it is possible even to distinguish between the closely related pathogenic and non-pathogenic Neisseria species.

The following Example should elucidate the invention further

EXAMPLE

With the aid of a slot-blot apparatus, chromosomal DNA of the following Neisseria species, each on a slot of the apparatus, was applied onto a nitrocellulose filter:

pathogenic *Neisseria species*

*N. gonorrhoeae:* 7 different isolates

N. meningitidis: 7 different isolates non-pathogenic *Neisseria species*

*N. lactamica, N. mucosa, N. subflava, N. perflava, N. sicca, N. elongata, N. cinerea, N. flava, N. denitrificans.* non-Nisseria species

Haemophilus influenzae, Haemophilus parainfluenzae, Streptococcus salivarius, Streptococcus mutans, Streptococcus agalactiae, Staphylococcus aureus, Staphylococcus epidermidis, Staphylococcus saprophyticus, Escherichia coli.

The preparation of the chromosomal DNAs was carried out according to the protocol described by Stern et al., Cell 37 (1984), page 447. To prepare chromosomal DNA from N. gonorrhoea MS11 variants, a single colony was seeded on standard plates with GC base (BBL) and cultured for 24 hr. The colony type of the variants was checked by stereomicroscopy for homogensity of the culture. Bacteria from two plates were collected and suspended in 10 ml 100 mM NaCl, 20 mM Tris Cl, (pH 7.5), and 1 mM EDTA. To this suspension approximately 10 μg lysozyme and 0.5 ml Triton X-100 (20%) were added and warmed to 37° C. To achieve complete lysis, 10 μg of proteinase K was added, and another 10 min incubation period followed. Thereafter, 10 g CsCl and 0.4 ml ethidium bromide (10 mg/ml) were added. The solution was centrifuged to equilirium in a fixed angle rotor, and the chromosomal DNA was collected, extracted with butanol, and dialyzed against 10 mM Tris Cl (pH 7.5), 1 mM EDTA.

The filters were clamped in the apparatus for this, a vacuum was applied and the individual application points were moistened with 200 μl 2x buffer (2x buffer: 2 mol/l NaCl, 50 mmol/l Tris-HCl, pH 7.5, 1 mmol/l EDTA). 50 mmol/l Tris-HCl, pH 7.5 and 5 mmol/l EDTA was added to the DNA and boiled for 3 minutes for the denaturation. Subsequently the preparation was transferred immediately onto ice, 50 μl 2x buffer was added and this solution was pipetted into the slots. The slots were rinsed with 100 μl 1x buffer (2x buffer, diluted 1:1 with water), the filter was removed from the apparatus and dried in a vacuum. The hybridization was carried out essentially according to the methods already described (Southern, J. Mol. Biol. 98 (1975), page 503).

In order to determine the species specificity, the synthesized nucleic acid probes were hybridized against the chromosomal DNAs from the different Neisseria species bound to the filter. For this the nitrocellulose filters were pre-hybridized for two hours in 1xVHP at 42° C. (2xVHP: 0.1% bovine serum albumin, 0.1% Ficoll 400000, 0.1% polyvinylpropylidone, 1% glycerol, 1.8 mol/l NaCl, 50 mmol/l Na$_2$HPO$_4$ and 10 mg/ml herring sperm DNA). The herring sperm DNA contained in the VHP was previously denatured by heating to 80° C.

The hybridization was carried out in a hybridization oven at 42° C. The pre-hybridization buffer was removed and replaced by the $^{32}$P-labelled oligonucleotide probe in hybridization buffer (HB) (HB: 1xVHP and addition of 0 to 30 % formamide depending on the GC content of the nucleic acid probe). The HB was heated to 80° C. before use. After a hybridization time of at least 6 hours the filters were washed in washing buffer (WB: 3.6 mol/l NaCl, 100 mmol/l Na$_2$HPO$_4$, 0.05 % SDS) at first twice at room temperature and then twice at 42° C. The wash temperature was then increased according to the GC content of the probe up to a maximum of 68° C. The actual maximum wash temperature as well as the formamide content are also shown in Table II. This Table also shows the sequences of the nucleic acid probes used.

TABLE II

| Notation Probe | Sequence 5' —> 3' | Wash temperature °C. | % formamide in the HB |
|---|---|---|---|
| PIII* | ccatttccctgtctgccaa | 50 | 15 |
| Pil 1* | aaccggctgtccgcagaa | 60 | 30 |
| Iga 2* | cggacggtgcacaaattg | 50 | 15 |
| Opa 1* | ctgcgctgcggaagagaagag | 60 | 30 |
| Opa 2* | gcggcccgtatgtgcagg | 68 | 30 |
| Iga 1* | cggtattacccggttgt | 50 | 15 |
| Opa 3* | gcagcccgtattatgtgc | 48 | 10 |

The filters were exposed against an X-ray film.

The results of the hybridization of different nucleic acid probes with pathogenic, non-pathogenic Neisseria species and non-Neisseria species are shown in Table III.

TABLE IIIa

Probes which are specific for pathogenic Neisseria species.

| Species/strains | | P III* | Pil 1* | IgA 2* | Opa 1* |
|---|---|---|---|---|---|
| Neisseria gonorrhoeae | 74 | + | + | + | + |
| | 514 | + | + | + | + |
| | 510 | + | + | + | + |
| | R2 | + | + | + | + |
| | R21 | + | + | + | + |
| | R16 | + | + | + | + |
| | MS11 | + | + | + | + |
| Neisseria meningitidis | B | + | + | + | + |
| | C | + | + | + | + |
| | D | + | + | + | + |
| | Y | + | + | + | + |
| | W | + | + | + | + |
| | Z | + | + | + | + |
| | 8213 | + | + | + | + |
| Neisseria lactamica | 1855 | − | − | [−] | + |
| Neisseria lactamica | 2879 | − | − | − | + |
| Neisseria lactamica | 3272 | − | − | − | + |
| Neisseria mucosa | 112 | − | − | − | − |
| Neisseria mucosa | 114 | − | − | − | − |
| Neisseria mucosa | 2888 | − | − | − | − |
| Neisseria subflava | 124 | − | − | − | − |
| Neisseria perflava | 120 | − | − | − | − |
| Neisseria sicca | 118 | − | − | − | − |
| Neisseria sicca | 2844 | − | − | − | − |
| Neisseria elongata | 129 | − | − | − | − |
| Neisseria cinerea | 126 | − | − | − | − |
| Neisseria cinerea | 2199 | − | − | − | − |
| Neisseria flava | 122 | − | − | − | − |
| Neisseria flava | 123 | − | − | − | + |
| Neisseria denitrificans | 2950 | − | − | − | − |
| Haemophilus influenzae | | − | − | − | − |
| Haemophilus parainfluenzae | | − | − | [−] | − |
| Streptococcus salivarius | | − | − | − | − |
| Streptococcus mutans | | − | − | − | − |
| Streptococcus agalactiae | | − | − | − | − |
| Staphylococus aureus | | − | − | − | − |
| Staphylococus epidermidis | | − | − | − | − |
| Staphylococus saprophyticus | | − | − | − | − |
| Escherichia coli | | − | − | − | − |

TABLE IIIb

Probes with the aid of which one can differentiate between N. gonorrhoeae and N. meningitidis.

| Species/strains | | nucleic acid probe (oligonucleotide) Opa 2* |
|---|---|---|
| Neisseria gonorrhoeae | 74 | + |
| | 514 | + |
| | 510 | + |
| | R2 | + |
| | R21 | + |
| | R16 | + |
| | MS11 | + |
| Neisseria meningitidis | B | − |
| | C | − |
| | D | − |
| | Y | − |
| | W | − |
| | Z | − |
| | 8213 | − |
| Neisseria lactamica | 1855 | + |
| Neisseria lactamica | 2879 | + |
| Neisseria lactamica | 3272 | + |
| Neisseria mucosa | 112 | − |
| Neisseria mucosa | 114 | − |
| Neisseria mucosa | 2888 | − |
| Neisseria subflava | 124 | + |
| Neisseria perflava | 120 | − |
| Neisseria sicca | 2844 | − |
| Neisseria sicca | 118 | + |

TABLE IIIb-continued

Probes with the aid of which one can differentiate between N. gonorrhoeae and N. meningitidis.

| Species/strains | | nucleic acid probe (oligonucleotide) Opa 2* |
|---|---|---|
| Neisseria elongata | 129 | − |
| Neisseria cinerea | 126 | − |
| Neisseria cinerea | 2199 | − |
| Neisseria flava | 122 | − |
| Neisseria flava | 123 | + |
| Neisseria denitrificans | 2950 | − |
| Haemophilus influenzae | | − |
| Haemophilus parainfluenzae | | − |
| Streptococcus salivarius | | − |
| Streptococcus mutans | | − |
| Streptococcus agalactiae | | − |
| Staphylococus aureus | | − |
| Staphylococus epidermidis | | − |
| Staphylococus saprophyticus | | −ʳ |
| Escherichia coli | | − |

TABLE IIIc

Probes which are specific for N. gonorrhoeae.

| Species/strains | | nucleic acid probe IgA 1* |
|---|---|---|
| Neisseria gonorrhoeae | 74 | + |
| | 514 | + |
| | 510 | + |
| | R2 | + |
| | R21 | + |
| | R16 | + |
| | MS11 | + |
| Neisseria meningitidis | B | − |
| | C | − |
| | D | − |
| | Y | − |
| | W | − |
| | Z | − |
| | 8213 | − |
| Neisseria lactamica | 1855 | − |
| Neisseria lactamica | 2879 | − |
| Neisseria lactamica | 3272 | − |
| Neisseria mucosa | 112 | − |
| Neisseria mucosa | 114 | − |
| Neisseria mucosa | 2888 | − |
| Neisseria subflava | 124 | − |
| Neisseria perflava | 120 | − |
| Neisseria sicca | 2844 | − |
| Neisseria sicca | 118 | − |
| Neisseria clongata | 129 | − |
| Neisseria cinerea | 126 | − |
| Neisseria cinerea | 2199 | − |
| Neisseria flava | 122 | − |
| Neisseria flava | 123 | − |
| Neisseria denitrificans | 2950 | − |
| Haemophilus influenzae | | − |
| Haemophilus parainfluenzae | | − |
| Streptococcus salivarius | | − |
| Streptococcus mutans | | − |
| Streptococcus agalactiae | | − |
| Staphylococus aureus | | − |
| Staphylococus epidermidis | | − |
| Staphylococus saprophyticus | | − |
| Escherichia coli | | − |

TABLE IIId

Probes which are specific for N. meningitidis

| Species/strains | | nucleic acid probe Opa 3* |
|---|---|---|
| Neisseria gonorrhoeae | 74 | − |
| | 514 | − |
| | 510 | − |
| | R2 | − |
| | R21 | − |
| | R16 | − |
| | MS11 | − |
| Neisseria meningitidis | B | + |
| | C | + |
| | D | + |
| | Y | + |
| | W | + |
| | Z | + |
| | 8213 | + |
| Neisseria lactamica | 1855 | − |
| Neisseria lactamica | 2879 | − |
| Neisseria lactamica | 3272 | − |
| Neisseria mucosa | 112 | − |
| Neisseria mucosa | 114 | − |
| Neisseria mucosa | 2888 | − |
| Neisseria subflava | 124 | − |
| Neisseria perflava | 120 | − |
| Neisseria sicca | 2844 | − |
| Neisseria sicca | 118 | − |
| Neisseria clongata | 129 | − |
| Neisseria cinerea | 126 | − |
| Neisseria cinerea | 2199 | − |
| Neisseria flava | 122 | − |
| Neisseria flava | 123 | − |
| Neisseria denitrificans | 2950 | − |
| Haemophilus influenzae | | − |
| Haemophilus parainfluenzae | | − |
| Streptococcus salivarius | | − |
| Streptococcus mutans | | − |
| Streptococcus agalactiae | | − |
| Staphylococus aureus | | − |
| Staphylococus epidermidis | | − |
| Staphylococus saprophyticus | | − |
| Escherichia coli | | − |

I claim:

1. A Neisseria-specific DNA probe which specifically binds to pathogenic species of Neisseria and not to non-pathogenic species thereof and which is selected from the group of oligonucleotides consisting of Opa1, Opa 3, PIII, Pil1, IgA1, IgA2 and sequences complementary to each of said oligonucleotides.

2. The probe according to claim 1, wherein said probe specifically binds to N. gonorrhoea and not to N. meningitidis and is the oligonucleotide IgA1.

3. The probe according to claim 1, wherein said probe specifically binds to N. meningitidis and not to N. gonorrhoea and is the oligonucletoide Opa3.

4. The probe according to claim 1, further having from 1 to 5 additional nucleotides at the 5' end and/or 3' end of said probe.

5. The probe according to claim 4, wherein said additional nucleotides correspond to the nucleotides at the 5' and/or 3' site in the natural gene from which the probes are derived from, said 5' and/or 3' site corresponding to the 5' and/or 3' end of said probe.

6. The probe according to claim 2 or 5, wherein said probe is selected from the group of oligonucleotides consisting of Opa1*, Opa3*, PIII*, Pil1*, IgA2* and sequences complementary to each of said oligonucleotides.

7. A Neisseria-specific DNA probe which specifically binds to the oligonucleotide N. gonorrhoea and not to the oligonucleotide N. meniningitidis and which is selected from the group of oligonucleotides consisting of Opa2 and a sequence complementary to Opa2.

8. The probe according to claim 7, further having from 1 to 5 additional nucleotides at the 5' end and/or 3' end of said probe.

9. The probe according to claim 8, wherein said additional nucleotides correspond to the nucleotides at the 5' and/or 3' site in the neutral gene from which the probes are derived from, said 5' and/or 3' site corresponding to the 5' and/or 3' end of said probe.

10. The probe according to claim 8 or 9, wherein said probe is selected from the group of oligonucleotides consisting of Opa2* and a sequence complementary to the oligonucleotide Opa2*.

11. The probe according to any of claims 1 to 10, wherein said probe is contained in a single or double-stranded vector.

12. The probe according to any of claims 1 to 10, wherein said probe is present in a labelled form.

13. A method for the detection of at least one of the pathogenic Neisseria species N. gonorrhoea and N. meningitidis using a hybridizing probe under hybridizing conditions and detection of hybrid formation, wherein a probe is used for the specific detection as claimed in any of claims 1 to 10.

14. The method according to claim 13, wherein at least one of the probes selected from the group of oligonucleotides consisting of PIII, Pil1, IgA2 and Opa1 is used for the combined detection of N. gonorrhoea and N. meningitidis.

15. The method according to claim 13, wherein at least one of the probes selected from the group of oligonucleotides consisting of PIII*, Pil1*, IgA2* and Opa1* is used for the combined detection of N. gonorrhoea and N. meningitidis.

16. The method according to claim 13, wherein at least one of the probes Opa2, IgA1, Opa2* and IgA1* is used for the sole detection of N. gonorrhoea.

17. The method according to claim 13, wherein the probe is selected from the group of oligonucleotides consisting of Opa3 and/or Opa3* is used for the sole detection of N. meningitidis.

18. The method according to claim 13, wherein the hybrid formation is detected via a labelling of the probe.

19. A method for the detection of the presence or absence of at least one of the pathogenic Neisseria species N. gonorrhoea and N. meningitids is a sample comprising:
adding to said sample at least one DNA probe selected from the group of oligonucleotides consisting of Opa1, Opa3, PIII, Pil1, IgA1, and IgA2 and sequences complementary to each of said oligonucleotides which specifically binds to pathogenic species of Neisseria and not to non-pathogenic species thereof, under hybridization conditions, and
detecting hybrid formation.

20. The method according to claim 19, wherein said probe is selected from the group of oligonucleotides consisting of PIII, Pil1, IgA2 and Opa1.

21. The method according to claim 19, wherein said probe has from 1 to 5 additional nucleotides at the 5' end and/or 3' end of said probe.

22. The method according to claim 21, wherein said additional nucleotides correspond to the nucleotides at the 5' and/or 3' site in the natural gene from which the probes are derived from, said 5' and/or 3' site corresponding to the 5' and/or 3' end of said probe.

23. The method according to claim 21 or 22, wherein said probe is selected from the group of oligonucleotides consisting of PIII*, Pil1*, IgA2*, Opa1* and sequences complementary to each of said oligonucleotides.

24. A method for the specific detection of the presence or absence of N. gonorrhoea in a sample comprising:
adding to said sample at least one DNA probe selected from the group of oligonucleotides consisting of IgA1, IgA1* and sequences complementary to each of said oligonuleotides which binds specifically to N. gonorrhoea and does not bind to N. meningitidis or to a non-pathogenic Neisseria species, under hybridization conditions, and
detecting hybrid formation.

25. A method for the specific detection of the presence or absence of N. meningitidis in a sample comprising:
adding to said sample at least one DNA probe selected from the group of oligonucleotides consisting of Opa3, Opa3* and sequences complementary to each of said oligonucleotides which binds specifically to N. meningitidis and does not bind to N. gonorrhoea or to a non-pathogenic Neisseria species, under hybridization conditions, and
detecting hybrid formation.

26. A method for the specific detection of the presence or absence of N. gonorrhoea in a sample that does not contain a non-pathogenic Neisseria species comprising:
adding to said sample at least on DNA probe selected from the group of oligonucleotides consisting of Opa2, Opa2* and sequences complementary to each of said oligonucleotides which binds specifically to N. gonorrhoea and does not bind to N. meningitidis, under hybridization conditions, and
detecting hybrid formation.

27. The method according to any of claims 18 to 25, wherein said hybrid formation is detected via labelling of said probe.

* * * * *